United States Patent
Doi et al.

(10) Patent No.: US 6,737,050 B2
(45) Date of Patent: May 18, 2004

(54) HAIR COSMETIC COMPOSITIONS

(75) Inventors: Yasuhiro Doi, Wakayama (JP); Keiko Hasebe, Wakayama (JP); Hiroyuki Masuda, Wakayama (JP); Tetsuaki Fukushima, Wakayama (JP); Uichiro Nishimoto, Wakayama (JP); Hiroshi Abe, Barcelona (ES)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/026,641

(22) Filed: Dec. 27, 2001

(65) Prior Publication Data

US 2002/0159966 A1 Oct. 31, 2002

(30) Foreign Application Priority Data

Dec. 28, 2000 (JP) ........................................ 2000-403422
Dec. 28, 2000 (JP) ........................................ 2000-403423

(51) Int. Cl.$^7$ .............................................. A61K 7/075
(52) U.S. Cl. ................................. 424/70.27; 424/70.79
(58) Field of Search ........................... 424/70.19, 70.27

(56) References Cited

U.S. PATENT DOCUMENTS

| | | | |
|---|---|---|---|
| 5,310,758 A | 5/1994 | Yorozu et al. | |
| 5,389,678 A | 2/1995 | Yorozu et al. | |
| 5,411,731 A | 5/1995 | Tanaka et al. | |
| 5,858,936 A | 1/1999 | Tamura et al. | |

FOREIGN PATENT DOCUMENTS

| | | |
|---|---|---|
| GB | 1 226 801 | 3/1971 |
| JP | 6-107524 | 4/1994 |
| JP | 06107524 | 4/1994 |
| JP | 6-178928 | 6/1994 |
| JP | 06178928 | 6/1994 |
| WO | WO 96-03483 | 2/1996 |

OTHER PUBLICATIONS

Harry's Cosmetocology By Ralph Harry, PP 506–512(1982).*
Database WPI, Section Ch, Week 199641, Derwent Publications, Ltd., London, Great Britain; AN 1996–408292 (XP 002225410).

* cited by examiner

*Primary Examiner*—Jyothsna Venkat
(74) *Attorney, Agent, or Firm*—Oblon, Spivak, McClelland, Maier & Neustadt, P.C.

(57) ABSTRACT

Provided are a hair cosmetic composition comprising an ether type cationic surfactant represented by the following formula (1):

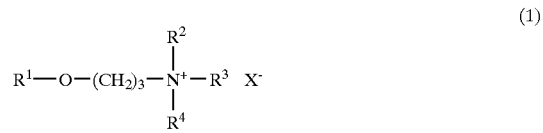

wherein, $R^1$ represents a linear or branched $C_{6-24}$ alkyl or alkenyl group, $R^2$ and $R^4$ each represents a $C_{1-6}$ alkyl group or —$(AO)_nH$ (A: a $C_{2-4}$ alkylene group, n: a number of from 1 to 6 with the proviso that n pieces of A may be the same or different and their sequence is optional), $R^3$ represents a $C_{1-6}$ alkyl group or —$(A'O)_mH$ (A': a $C_{2-4}$ alkylene group, m: a number of from 1 to 6 with the proviso that m pieces of A may be the same or different and their sequence is optional), and $X^-$ represents an anion; a hair cleansing composition containing the cationic surfactant(1); and a method of treating hair with these compositions.

The hair cosmetic composition of the present invention can impart good flexibility and smoothness to hair not only when it is wetted but also after drying. When used as a hair cleansing composition, it provides excellent quality of foam and feeling upon use and exhibits good low-temperature stability.

21 Claims, No Drawings

HAIR COSMETIC COMPOSITIONS

TECHNICAL FIELD

The present invention relates to hair cosmetic compositions capable of imparting good flexibility and smoothness to hair not only when it is wetted but also after drying, particularly imparting good smoothness to hair after drying.

BACKGROUND ART

Hair cosmetic compositions are requested to give flexibility and smoothness to hair not only when it is wetted but also after drying. To satisfy this request, a quaternary ammonium salt such as stearyltrimethylammonium chloride, behenyltrimethylammonium chloride or distearyldimethylammonium chloride has been used as a cationic surfactant. Such addition, however, did not succeed in the preparation of satisfactory hair cosmetic compositions.

Although a di(long-chain alkyl) quaternary ammonium salt such as distearyldimethylammonium chloride has been incorporated to improve the flexibility of hair when it is wetted, the hair treated with the resulting composition has poor smoothness after drying and its touch becomes heavier. Processes using a variety of additives such as silicone to improve the smoothness of hair after drying are known. These additives however adversely affect the stability of the system, which requires adjustment of their amount or makes the blending itself cumbersome. Japanese Patent Applications Laid-Open Nos.6-107524 and 6-178928, disclose hair treatment compositions using an ethylene oxide-adduct type quaternary ammonium salt. They are however accompanied by the problems that the number of moles of ethylene oxide is not always uniform in the preparation thereof and adducts having the same number of moles of ethylene oxide cannot be obtained easily. In addition, adducts having two or more moles of ethylene oxide have an adverse effect on the performance of the composition.

Hair cleansing compositions contain the above-described long-chain alkyl quaternary ammonium salt. They are however accompanied by the drawback owing to the restriction in formulation in that the quality of foams or low-temperature stability lowers when a long-chain alkyl quaternary ammonium salt is added in an amount sufficient to give satisfactory hair smoothness.

DISCLOSURE OF THE INVENTION

An object of the present invention is to provide a hair cosmetic composition capable of imparting good flexibility and smoothness to hair not only when it is wetted but also after drying. Particularly, an object of the present invention is to provide a hair cosmetic composition other than the below-described hair cleansing composition.

Another object of the present invention is to provide a hair cleansing composition which is capable of providing hair with the good flexibility and smoothness, and in addition, is excellent in quality of foams during cleansing and in low-temperature stability.

The present inventors have found that a hair cosmetic composition capable of satisfying the above-described objects can be obtained by using a specific ether-type cationic surfactant.

In one aspect of the present invention, there is thus provided a hair cosmetic composition comprising an ether type cationic surfactant represented by the formula (1):

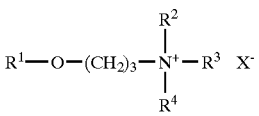

wherein, $R^1$ represents a linear or branched $C_{6-24}$ alkyl or alkenyl group, $R^2$ and $R^4$ each independently represents a $C_{1-6}$ alkyl group or $-(AO)_nH$ (in which A represents a $C_{2-4}$ alkylene group and n stands for a number of from 1 to 6 with the proviso that n pieces of A may be the same or different and their sequence is optional), $R^3$ represents a $C_{1-6}$ alkyl group, a benzyl group or $-(A'O)_mH$ (in which A' represents a $C_{2-4}$ alkylene group and m stands for a number of from 1 to 6 with the proviso that m pieces of A' may be the same or different and their sequence is optional), and $X^-$ represents an anion].

In another aspect of the present invention, there is also provided a hair cleansing composition comprising (a) an ether type cationic surfactant represented by the formula (1), and (b) at least one surfactant selected from anionic surfactants, nonionic surfactants and amphoteric surfactants.

In a further aspect of the present invention, there is also provided a method for treating hair with the above-described hair cosmetic composition containing the ether type cationic surfactant of the formula (1).

In a still further aspect of the present invention, there is also provided a method for cleansing hair with the above-described hair cleansing composition comprising the components (a) and (b).

In a still further aspect of the present invention, there is also provided a method for applying to hair the hair cleansing composition comprising the components (a) and (b).

BEST MODE FOR CARRYING OUT THE INVENTION

In the above-described formula (1), $R^1$ is preferably a linear or branched alkyl or alkenyl group having 12 to 22, especially 16 to 18 carbon atoms, with a linear alkyl group being more preferred.

$R^2$ and $R^4$ are preferably a $C_{1-6}$ alkyl group or a group $-(CH_2CH_2O)_nH$, wherein n is preferably 1 to 3, especially 1. More preferably, $R^2$ and $R^4$ are a $C_{1-2}$ alkyl group, and methyl and ethyl groups are particularly preferred, with a methyl group being most preferred.

$R^3$ is preferably methyl, ethyl or benzyl group, more preferably methyl or ethyl group, most preferably methyl group.

As $X^-$, halide ions and ethyl sulfate ions are usable, with chloride ion being particularly preferred.

The ether type cationic surfactant (1) can be prepared, for example, in accordance with the following reaction scheme:

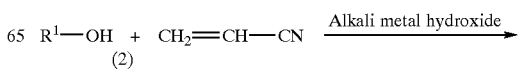

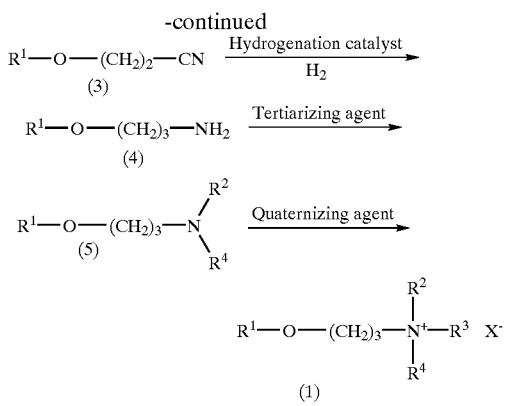

wherein, $R^1$, $R^2$, $R^3$ and $R^4$ have the same meanings as defined above.

Specifically, at first, alkoxypropylamine(4) is prepared by reacting an alcohol(2) with acrylonitrile in the presence of an alkali metal hydroxide, and hydrogenating the resulting alkoxypropionitrile(3) by using a hydrogenation catalyst. Then the resulting alkoxypropylamine(4) is reacted with a tertiarizing agent (combination of formaldehyde or an alkyl aldehyde of 2 to 6 total carbon atoms with hydrogen, or a $C_{2-4}$ alkylene oxide) in the presence of a catalyst and then the resulting tertiary amine(5) is reacted with a quaternizing agent in a proper solvent to give the ether type cationic surfactant(1).

The amount of the ether type cationic surfactant (1) in the hair cosmetic composition of the present invention is preferably 0.1 to 20 wt. %, because it can impart hair with sufficient flexibility and smoothness and does not cause precipitation, caking or layer separation upon storage, thus making it possible to provide a product having good stability. The content of 1 to 10 wt. % is particularly preferred in the case of a rinse-off composition such as a hair rinse or a hair conditioner, while the content of 0.2 to 5 wt. % is particularly preferred in the case of a leave-in composition such as a hair treatment or a hair liquid.

The hair cosmetic composition of the present invention may contain a surfactant other than the ether type cationic surfactant(1). As the other surfactant, at least one surfactant selected from cationic surfactants other than the ether type cationic surfactants(1), anionic surfactants, nonionic surfactants and amphoteric surfactants can be used. Among them, cationic surfactants are preferred in view of enhancing touch feel.

Particularly preferred as the cationic surfactant other than the ether type cationic surfactant(1) are quaternary ammonium salts described in Japanese Patent Application Laid-Open No. 2000-178146 and represented by the following formula (6):

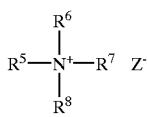

(6)

wherein, at least one of $R^5$, $R^6$, $R^7$ and $R^8$ represents an alkyl or alkenyl group which may be substituted with an alkoxy, alkenyloxy, alkanoylamino or alkenoylamino group having in total 8 to 28 carbon atoms, while the remaining group(s) each represents benzyl group, a $C_{1-5}$ alkyl group, a hydroxyalkyl group or a polyoxyethylene group having a total molar addition number of not greater than 10, and $Z^-$ represents a halogen ion or an organic anion.

Among the above-described compound(6), preferred are those in which at least one of $R^5$, $R^6$, $R^7$ and $R^8$ is an alkyl group which may be substituted with an alkoxy group having in total 8 to 22 carbon atoms and the remaining group(s) is(are) a methyl, ethyl or benzyl group. More preferred examples include mono(long-chain alkyl) trimethylammonium chloride and di(long-chain alkyl) dimethylammonium chloride.

As the above-described anionic surfactant, sulfates, sulfonates, caboxylates, phosphates and amino acids are preferred. Specific examples thereof include alkyl sulfates, polyoxyalkylene alkyl ether sulfates, polyoxyalkylene alkenyl ether sulfates, alkyl sulfosuccinates, polyoxyalkylene alkyl sulfosuccinates, polyoxyalkylene alkyl phenyl ether sulfates, alkanesulfonates, acyl isethionates, acyl methyl taurates, higher fatty acid salts, polyoxyalkylene alkyl ether acetates, alkyl phosphates, polyoxyalkylene alkyl ether phosphates, acyl glutamates, alanine derivatives, glycine derivatives and arginine derivatives.

Among these, polyoxyethylene alkyl ether sulfates, polyoxyethylene alkenyl ether sulfates, alkyl sulfates, alkyl acyl isethionates, alkyl acyl methyl taurates, higher fatty acid salts, polyoxyalkylene alkyl ether acetates, alkyl phosphates, polyoxyalkylene alkyl ether phosphates, alkyl acyl glutamates and alkyl alanine derivatives are preferred, with those represented by the formula (7) or (8) being especially preferred.

wherein, $R^9$ represents a $C_{10-18}$ alkyl or alkenyl group, $R^{10}$ represents a $C_{10-18}$ alkyl group, M represents an alkali metal, alkaline earth metal, ammonium, alkanolamine or basic amino acid, and p stands for an average molar addition number of ethylene oxide and is a number of from 1 to 5.

Preferred examples of the nonionic surfactant include polyoxyalkylene sorbitan fatty acid esters, polyoxyalkylene sorbitol fatty acid esters, polyoxyalkylene glycerin fatty acid esters, polyoxyalkylene fatty acid esters, polyoxyalkylene alkyl ethers, polyoxyalkylene alkylphenyl ethers, polyoxyalkylene (hydrogenated) castor oils, sucrose fatty acid esters, polyglycerin alkyl ethers, polyglycerin fatty acid esters, fatty acid alkanolamides and alkyl glycosides. Of these, alkyl glycosides, polyoxyalkylene $C_{8-20}$ fatty acid esters, polyoxyethylene sorbitan fatty acid esters, polyoxyethylene hydrogenated castor oils and fatty acid alkanolamides are preferred. As alkyl glycosides, those having a $C_{8-14}$ alkyl group and a glucose condensation degree of 1 to 2 are preferred. As the fatty acid alkanolamides, those having a $C_{8-18}$, especially $C_{10-16}$ acyl group are preferred. They may be a monoalkanolamide or dialkanolamide. Those having a $C_{2-3}$ hydroxyalkyl group are also preferred. Specific examples of the fatty acid alkanolamide include oleic diethanolamide, palm-kernel fatty acid diethanolamide, coconut fatty acid diethanolamide, lauric diethanolamide, polyoxyethylene coconut fatty acid monoethanolamide, coconut fatty acid monoethanolamide, lauric monoisopropanolamide, lauric monoethanolamide, palm-kernel fatty acid methyl ethanolamide and coconut fatty acid methyl ethanolamide.

As the amphoteric surfactant, betaine surfactants are preferred, and imidazoline betaines, alkyldimethylamino acetic acid betaines, fatty acid amide propylbetaines and alkyl hydroxy sulfobetaines are more preferred, with alkylcarboxymethylhydroxyethyl imidazolium betaines, fatty acid amidopropylbetaines and alkyl hydroxy sulfobetaines being particularly preferred. Fatty acid amidopropylbetaines and alkyl hydroxy sulfobetaines having a $C_{8-18}$, especially $C_{10-16}$ alkyl group are preferred, of which lauric amidopropylbetaine, palm-kernel fatty acid amidopropylbetaines, coconut fatty acid amidopropylbetaines and lauryl hydroxy sulfobetaine are still more preferred.

The ratio (weight ratio) of the ether type cationic surfactant (1) to the other cationic surfactant is preferably ¼ or more from the viewpoint of smoothness after drying, with ½ to 10/1, being more preferred and 1/1 to 4/1 being especially preferred.

The hair cosmetic composition of the present invention may further contain an oil component. Examples of the oil component include higher alcohols, ester oils, silicones, hydrocarbons and glycerides, of which higher alcohols, ester oils and/or silicones are preferred, with higher alcohols and/or silicones being particularly preferred.

The higher alcohols include those having a linear or branched alkyl or alkenyl group, preferably those having a linear or branched $C_{12-26}$ alkyl or alkenyl group. More preferred examples thereof include cetanol, cetyl alcohol, stearyl alcohol, aralkyl alcohol, behenyl alcohol, caranaubyl alcohol and ceryl alcohol. Of these, cetanol, cetyl alcohol, stearyl alcohol and behenyl alcohol are particularly preferred. The "cetanol" as used herein is composed mainly of a cetyl alcohol and contains a higher alcohol such as stearyl alcohol or oleyl alcohol.

As the ester oil, ester oils having 8 to 48 total carbon atoms, preferably, lower alcohol (having 1 to 4 carbon atoms) esters of a $C_{8-40}$ fatty acid may be mentioned by way of example. Among these, isopropyl palmitate and isopropyl myristate are particularly preferred.

Examples of the silicones include (A) dimethylpolysiloxane, (B) methylphenylpolysiloxane, (C) amino-modified silicones [preferably, those having an average molecular weight of about 3000 to 100000 and described under the tradename "Amodimethicone" in CTFA Dictionary (USA, Cosmetic Ingredient Dictionary), the 3rd edition. Examples of aqueous emulsions thereof include "SM8704C" (product of Toray Dow Corning Silicone Co. Ltd.) and "DC939" (product of Toray Dow Corning Silicone Co. Ltd.)], (D) fatty acid-modified polysiloxanes, (E) alcohol-modified silicones, (F) aliphatic alcohol-modified polysiloxanes, (G) polyether-modified silicones, (H) epoxy-modified silicones, (I) fluorine-modified silicones, (J) cyclic silicones, and (K) alkyl-modified silicones.

When the hair cosmetic composition of the present invention is a rinse-off type composition such as a hair rinse or a hair conditioner, the silicones (A), (C), (F), (G) and (J) are preferably used, while in the case of a leave-in type composition such as a hair cream or a leave-on-treatment, the silicones (A), (B), (C), (G) and (J) are preferably used.

The content of the oil component in the hair cosmetic composition of the present invention is preferably 0.1 to 30 wt. %, more preferably 0.2 to 20 wt. %, especially 1 to 20 wt. % in view of providing a hair flexibility and moistness peculiar to the oil component and also providing a stable product. Above all, addition of the silicone in an amount of 0.01 to 20 wt. %, especially 0.1 to 10 wt. % is preferred, because feeling or touch peculiar to silicones can be imparted to the hair and a stable product is available.

In the present invention, the weight ratio of the ether type cationic surfactant(1)/the oil component preferably ranges from 10/1 to 1/10, especially from 1/1 to 1/10 from the viewpoint of emulsifying stability of the oil component. A weight ratio of the sum of the ether type cationic surfactant (1) and the oil component other than the silicone/the silicone preferably ranges from 10/1 to 1/10, especially 10/1 to 1/1 from the viewpoint of the stability of a product.

Although no particular limitation is imposed on the pH of the hair cosmetic composition of the present invention, the pH (at 25.C) of the composition diluted 20-folds with water is preferably 2 to 8, especially 3 to 6. The pH may be adjusted with an acid or an alkali.

When the hair cosmetic composition of the present invention is particularly a hair cleansing composition, it can contain (a) an ether type cationic surfactant represented by the formula(1), and (b) at least one surfactant selected from anionic surfactants, nonionic surfactants and amphoteric surfactants. In addition, a cationic surfactant other than the component (a) may be incorporated. Specific examples of the surfactants are similar to those described above.

In the case of a hair cleansing composition, the content of the ether type cationic surfactant (1) is preferably 0.1 to 20 wt. %, more preferably 0.2 to 10 wt. %, and particularly 0.5 to 5 wt. % from the viewpoint of the quality of foam and improvement in stability. The content(s) of the anionic surfactant, nonionic surfactant and/or amphoteric surfactant is(are) preferably 0.1 to 50 wt. %, more preferably 0.5 to 30 wt. %, particularly 5 to 20 wt. % from the viewpoint of improvement in foamability and feeling upon use.

The ratio (weight ratio) of "the ether type cationic surfactant(1)/the anionic surfactant, nonionic surfactant and/or amphoteric surfactant" is preferably 1/1 to 1/100, more preferably ½ to 1/80 from the viewpoint of improvement in the quality of foam and stability.

An oil component can be added to the hair cleansing composition of the present invention and those exemplified above are usable.

The pH of the hair cleansing composition of the present invention is not particularly limited, but the pH (at 25° C.) of the composition diluted 10-folds with water is preferably 4 to 10, more preferably 5 to 8. The pH may be adjusted with an acid or an alkali.

The hair cosmetic composition of the present invention can be added with additives other than the above-described oil component, as needed. Examples thereof include vegetable oils, animal oils, lanoline derivatives, higher fatty acid esters, higher fatty acids, glycerin, humectants, cationic polymers, polysaccharides, polypeptides, pearlescent agents, solvents, liquid-crystal forming bases, aromatic sulfonic acids, colorants, perfumes, propellants, chelating agents, pH regulators, antiseptics and anti-dandruffs. Specific examples of the vegetable oils include camellia oil, Macadamia nut oil, mink oil, olive oil, safflower oil, soybean oil and jojoba oil. Those of the cationic polymer include cationic cellulose derivatives, cationic starch and cationic guar gum derivatives. Those of the antidandruff include zinc pyrithione and piroctone olamine.

The hair cosmetic composition of the present invention can be prepared according to a conventional manner to a desired preparation such as aqueous solution, ethanol solution, emulsion, suspension, gel, liquid crystal, solid, aerosol foam or spray. The hair cleansing composition can be provided as a hair shampoo and the like. Examples of the products of the hair cosmetic composition other than the hair cleansing composition include hair rinses, hair conditioners, hair treatments, hair packs, hair creams, hair colors, conditioning mousses, hair mousses, hair sprays, leave-on-treatments, waxes and tonics.

The present invention embraces the following embodiments (1) to (8):

(1) The hair cosmetic composition containing 0.1 to 20 wt. % of an ether type cationic surfactant represented by the formula (1).

(2) The hair cosmetic composition according to embodiment (1) further containing a surfactant other than the compound of the formula (1).

(3) The hair cosmetic composition according to embodiment (2), wherein the surfactant other than the compound of the formula (1) is at least one selected from cationic, anionic, nonionic and amphoteric surfactants.

(4) The hair cosmetic composition according to embodiment (3), wherein the surfactant other than the compound of the formula (1) is a cationic surfactant.

(5) The hair cosmetic composition comprising the ether type cationic surfactant of the formula (1) and an oil component.

(6) The hair cleansing composition comprising (a) an ether type cationic surfactant represented by the formula (1), (b) at least one surfactant selected from anionic, nonionic and amphoteric surfactants, and a cationic surfactant other than the component (a).

(7) The hair cleansing composition according to embodiment (6), wherein the content of component (b) is 0.1 to 50 wt. % and a ratio (a)/(b) ranges from 1/1 to 1/100.

(8) The hair cleansing composition according to embodiment (6) or (7), further comprising an oil component.

The present invention will hereinafter be described in further detail by way of examples.

EXAMPLE 1

Hair conditioners (invention products 1 to 9, and comparative products 1 to 3) having the composition as shown in Table 2 were prepared in a manner known per se in the art by using ether type cationic surfactants 1 to 4 prepared according to the method described herein and another cationic surfactant as shown in Table 1. Flexibility and smoothness of each of these hair conditioners was subjected to organoleptic evaluation. Numerals in Table 2 are by wt. %.

The ether type cationic surfactants 1 to 4 as shown in Table 1 are preferably prepared in accordance with the method as described herein.

<Evaluation Method>

A bundle (20 cm long, 20 g) of the Japanese female hair, which had been subjected to cold permanent waving in advance, was cleansed with a commercially available shampoo composed mainly of an anionic surfactant. To the resulting hair bundle, 1.0 g of a hair conditioner was applied uniformly, followed by rinsing with running water of 40.C for 30 seconds. Flexibility and smoothness of the hair upon rinsing, and those of the hair after sufficient drying first with a towel and then by a drier were evaluated through touch feel by a panel of 5 experts in accordance with the following standards.

4: excellent
3: good
2: neither good nor bad
1: bad

An average value of five experts was calculated. The hair conditioner of 3.6 or greater was rated as A, that of 2.6 to 3.4 was rated as B, that of 1.6 to 2.4 was rated as C, and that of 1.4 or less was rated as D. The results are shown in Table 2.

TABLE 1

| Ether type cationic surfactant | Formula (1) | | | |
|---|---|---|---|---|
| | $R^1$ (each, linear) | $R^2$ | $R^3$ | $R^4$ | $X-$ |
| 1 | $C_{16}H_{33}/C_{18}H_{37}$ = 50/50 (wt.%) | $CH_3$ | $CH_3$ | $CH_3$ | $Cl-$ |
| 2 | $C_{16}H_{33}$ | $CH_3$ | $CH_2CH_3$ | $CH_3$ | $CH_3CH_2OSO_3-$ |
| 3 | $C_{18}H_{37}$ | $CH_3$ | $CH_3$ | $CH_3$ | $Cl-$ |
| 4 | $C_{18}H_{37}$ | $CH_2CH_2OH$ | $CH_3$ | $CH_2CH_2OH$ | $Cl-$ |

TABLE 2

| | Invention product | | | | | | | | | Comparative products | | |
|---|---|---|---|---|---|---|---|---|---|---|---|---|
| | 1 | 2 | 3 | 4 | 5 | 6 | 7 | 8 | 9 | 1 | 2 | 3 |
| Ether type cationic surfactant 1 | 1.2 | | | | | | 1.5 | | | | | |
| Ether type cationic surfactant 2 | | 2.0 | | | | | | | | | | |
| Ether type cationic surfactant 3 | | | 1.5 | 1.0 | 1.0 | | | 1.5 | 1.8 | | | |
| Ether type cationic surfactant 4 | | | | | | 1.2 | | | | | | |
| Cetyltrimethylammonium chloride | | | | 1.0 | | | | | | 1.5 | 1.2 | 1.8 |
| Behenyltrimethylammonium chloride | | | | | 1.0 | | | | | | | |
| Cetanol* | 3.0 | 5.0 | 4.5 | 3.5 | 4.5 | 3.0 | 3.5 | | | 4.5 | 3.0 | |
| Behenyl alcohol | | | | | | | | 3.0 | | | | |
| Methylpolysiloxane (500 cs) | 1.0 | | | | | 1.0 | | | | | | 1.0 |
| Amino-modified silicone** | | | | | | | | | 2.0 | | | |
| pH regulator | q.s. | q.s. | q.s. | q.s. | q.s. | q.s. | q.s. | q.s. | q.s. | q.s. | q.s. | q.s. |
| Purified water | Balance | Balance | Balance | Balance | Balance | Balance | Balance | Balance | Balance | Balance | Balance | Balance |

TABLE 2-continued

|  | Invention product | | | | | | | | | Comparative products | | |
| --- | --- | --- | --- | --- | --- | --- | --- | --- | --- | --- | --- | --- |
|  | 1 | 2 | 3 | 4 | 5 | 6 | 7 | 8 | 9 | 1 | 2 | 3 |
| pH (diluted 20-folds with water, 25° C.) |  |  |  |  |  |  | 3.5 | 4.0 | 4.0 |  |  | 4.0 |
| Evaluation results |  |  |  |  |  |  |  |  |  |  |  |  |
| Upon wetting |  |  |  |  |  |  |  |  |  |  |  |  |
| Flexibility | B | A | B | B | A | B | B | A | B | C | C | C |
| Smoothness | A | B | A | A | A | B | A | B | B | C | C | D |
| After drying |  |  |  |  |  |  |  |  |  |  |  |  |
| Flexibility | B | B | A | A | A | A | B | B | B | D | C | D |
| Smoothness | A | A | A | A | A | A | A | A | A | D | C | D |

*A 7/3 (weight ratio) cetyl alcohol/stearyl alcohol mixture. This will equally apply to hereinafter.
***"SM8704C" (product of Toray Dow Corning Silicone)

EXAMPLE 2

A hair rinse having the following composition was prepared.

|  | (wt. %) |
| --- | --- |
| Ether type cationic surfactant 1 | 1.3 |
| Cetanol | 2.1 |
| Isopropyl palmitate | 1.0 |
| Dimethylpolysiloxane (500 cs)* | 0.5 |
| Propylene glycol | 3.5 |
| Hydroxyethyl cellulose | 0.5 |
| Denatured alcohol | 2.0 |
| Perfume, methylparaben | q.s. |
| Purified water | Balance |
| Total | 100.0 |

*"SH200C", product of Toray Dow Corning Silicone

The rinse thus prepared was found to give good flexibility and smoothness to the hair not only when it was wetted but also after drying.

EXAMPLE 3

A hair rinse having the following composition was prepared.

|  | (wt. %) |
| --- | --- |
| Ether type cationic surfactant 2 | 1.0 |
| Cetanol | 3.0 |
| Isopropyl palmitate | 2.0 |
| Propylene glycol | 2.0 |
| Hydroxyethyl cellulose | 0.2 |
| 50 wt. % aqueous solution of citric acid | 0.2 |
| Perfume, methylparaben | q.s. |
| Purified water | Balance |
| Total | 100.0 |

This rinse was found to impart good flexibility and smoothness to the hair not only when it was wetted but also after drying. Particularly after drying, the hair treated with this rinse was excellent in smoothness without greasiness.

EXAMPLE 4

A leave-in hair treatment having the following composition was prepared.

|  | (wt. %) |
| --- | --- |
| Ether type cationic surfactant 3 | 0.8 |
| Cationic cellulose* | 0.2 |
| Cetanol | 3.0 |
| Diethylene glycol ether | 5.0 |
| Isopropyl myristate | 1.0 |
| Perfume, methylparaben | q.s. |
| Purified water | Balance |
| Total | 100.0 |

*"JR400", product of UCC

This hair treatment was found to impart good flexibility and smoothness to the hair not only when it was wetted but also after drying. Particularly after drying, the hair treated with it was excellent in smoothness without greasiness.

EXAMPLE 5

A hair tonic having the following composition was prepared.

|  | (wt. %) |
| --- | --- |
| Ether type cationic surfactant 3 | 0.2 |
| l-menthol | 0.2 |
| Polyoxyethylene hydrogenated castor oil | 0.8 |
| dl-.-tocopherol acetate | 0.05 |
| Denatured alcohol | 55.0 |
| Perfume, methylparaben | q.s. |
| Purified water | Balance |
| Total | 100.0 |

This hair tonic was found to impart the hair with good flexibility and smoothness and be excellent in feeling upon use.

EXAMPLE 6

Hair shampoos having the compositions as shown in Table 3 (Invention products 9 to 14 and Comparative Products 3 and 4) were prepared in a manner known per se in the art by using ether type cationic surfactants 1 to 4 as shown in Table 1 and another cationic surfactant. Their feeling upon use and low-temperature stability were evaluated by the below-described methods. Numerals in Table 3 were by wt. %.

<Evaluation Method>
(Feeling upon use)

To 20 g of a bundle (20 cm long) of the Japanese female hair which had been subjected to cold permanent waving in advance, 1 g of the hair shampoo was applied. After making lather with it for 30 seconds and then rinsing, the hair was dried with a towel and then by a drier. The quality of foams, touch feel upon washing, touch feel upon drying and styling ease of the hair were subjected to organoleptic evaluation by a panel of 5 experts in accordance with the following standards.

4: excellent
3: good
2: neither good nor bad
1: bad

An average value of five experts was calculated and, the hair shampoo of 3.6 or greater was rated as A, that of 2.6 to 3.4 was rated as B, that of 1.6 to 2.4 was rated as C, and that of 1.4 or less was rated as D. The results are shown in Table 3.

(Low-temperature Stability)

In a bottle with a lid (made of plastic) having an inner diameter of 0.3 cm and height of 7.5 cm, 50 g of the hair shampoo was charged. After hermetic sealing, it was allowed to stand at 0° C. for 24 hours. The appearance of it was then evaluated in accordance with the following standards:

A: transparent without change
B: turbidity or precipitation was observed.

EXAMPLE 7

The hair shampoo having the following composition was prepared

|  | (wt. %) |
|---|---|
| Ether type cationic surfactant 3 | 0.5 |
| Sodium polyoxyethylene (3) lauryl ether sulfate | 15.0 |
| Lauric diethanolamide | 2.0 |
| Cationic polymer | 0.5 |
| ("Merquat 550", product of Calgon Corp.) | |
| Hydroxysulfobetaine | 3.5 |
| Denatured alcohol | 2.0 |
| Perfume, methylparaben | q.s. |
| Purified water | Balance |
| Total | 100.0 |

The resulting hair shampoo was excellent in the quality of foams, and touch feel upon shampooing and also that after drying.

Industrial Applicability

The hair cosmetic compositions of the present invention are capable of imparting good flexibility and smoothness to the hair not only when it is wetted but also after drying. In particular, the hair treated with them is excellent in smoothness after drying. When they are used as a hair cleansing composition, they are excellent in the quality of foams and feeling upon use and at the same time, has good low-temperature stability.

What is claimed is:
1. A hair cosmetic composition, comprising:
an ether functional group containing cationic surfactant represented by formula (1):

TABLE 3

|  | Invention products |  |  |  |  |  | Comparative products |  |
|---|---|---|---|---|---|---|---|---|
|  | 9 | 10 | 11 | 12 | 13 | 14 | 3 | 4 |
| Ether type cationic surfactant 1 | 0.8 | — | — | — | — | — | — | — |
| Ether type cationic surfactant 2 | — | 0.5 | — | — | — | — | — | — |
| Ether type cationic surfactant 3 | — | — | 0.5 | 0.3 | 0.8 | — | — | — |
| Ether type cationic surfactant 4 | — | — | — | — | — | 0.5 | — | — |
| Behenytrimethylammonium chloride | — | — | — | 0.2 | — | — | 0.5 | — |
| Sodium polyoxyethylene (2) lauryl ether sulfate | 10.0 | 15.0 | 15.0 | 15.0 | — | 10.0 | 15.0 | 15.0 |
| Sodium polyoxyethylene (4.5) lauryl ether acetate | 5.0 | — | — | — | 15.0 | — | — | — |
| Lauric diethanolamide | — | 2.0 | 2.5 | 3.0 | — | 2.0 | 3.0 | 2.0 |
| Coconut oil amidopropylbetaine | 2.0 | — | — | — | 5.0 | 1.0 | — | — |
| Lauryl polyglycoside (average polymerization degree: 1.3) | | | | | | | | |
| Purified water | Balance | | | | | | | |
| Evaluation | | | | | | | | |
| Quality of foams | B | B | A | A | B | B | C | B |
| Touch feel upon shampooing | B | B | B | A | B | B | B | D |
| Touch feel after drying | A | A | A | A | A | A | C | D |
| Styling ease | A | A | B | A | A | B | C | D |
| Low temperature stability | A | A | A | A | A | A | B | A |

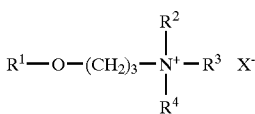

wherein,
$R^1$ represents a linear or branched $C_{6-24}$ alkyl or alkenyl group,
$R^2$ and $R^4$ each represents a $C_{1-6}$ alkyl group or $-(AO)_nH$ in which A represents a $C_{2-4}$ alkylene group and n is a number from 1 to 6 wherein individual A radicals are the same or different and are in any sequence,
$R^3$ represents a $C_{1-6}$ alkyl group, a benzyl group or $-(A'O)_mH$ in which A' represents a $C_{2-4}$ alkylene group and m is a number from 1 to 6 wherein individual A' radicals are the same or different and are in any sequence, and
$X^-$ represents an anion.

2. The hair cosmetic composition of claim 1, which contains the ether functional group containing cationic surfactant of formula (1) in an amount of 0.1 to 2 wt %.

3. The hair cosmetic composition of claim 1, further comprising a surfactant other than the compound of formula (1).

4. The hair cosmetic composition of claim 3, wherein the surfactant other than the compound of formula (1) is at least one surfactant selected from the group consisting of cationic, anionic, nonionic and amphoteric surfactants.

5. The hair cosmetic composition of claim 4, wherein the surfactant other than the compound of formula (1) is a cationic surfactant.

6. The hair cosmetic composition of any one of claims 1 to 5, further comprising an oil component.

7. A hair cleansing composition, which comprises:
(a) an ether functional group containing cationic surfactant represented by formula (1):

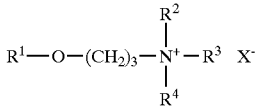

wherein
$R^1$ represents a linear or branched $C_{6-24}$ alkyl or alkenyl group,
$R^2$ and $R^4$ each represents a $C_{1-6}$ alkyl group or $-(AO)_nH$ in which A represents a $C_{2-4}$ alkylene group and n is a number from 1 to 6 wherein individual A radicals are the same or different and are in any sequence,
$R^3$ represents a $C_{1-6}$ alkyl group, a benzyl group or $-(A'O)_m$ in which A' represents a $C_{2-4}$ alkylene group and m is a number from 1 to 6 wherein individual A' radicals are the same or different and are in any sequence, and
$X^-$ represents an anion; and
(b) at least one surfactant selected from the group consisting of cationic, anionic, nonionic and amphoteric surfactants.

8. The hair cleansing composition of claim 7, further comprising a cationic surfactant other than component (a).

9. The hair cleansing composition of claim 7, wherein the content of (b) is 0.1 to 50 wt % and the ratio (a)/(b) ranges from 1/1 to 1/100.

10. The hair cleansing composition of any one of claims 7 to 9, further comprising an oil component.

11. A method for treating hair, comprising:
applying a hair cosmetic composition comprising (a) an ether functional group containing cationic surfactant represented by formula (1):

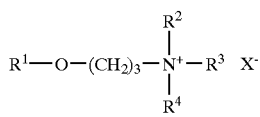

wherein,
$R^{1'}$ represents a linear or branched $C_{6-24}$ alkyl or alkenyl group,
$R^2$ and $R^4$ each represents a $C_{1-6}$ alkyl group or $-(AO)_nH$ in which A represents a $C_{2-4}$ alkylene group and n is a number from 1 to 6 wherein individual A radicals are the same or different and are in any sequence,
$R^3$ represents a $C_{1-6}$ alkyl group, benzyl group or $-(A'O)_mH$ in which A' represents a $C_{2-4}$ alkylene group and m is a number from 1 to 6 wherein individual A' radicals are the same or different and are in any sequence, and
$X^-$ represents an anion, to the hair.

12. The method of claim 11, wherein the ether functional group containing cationic surfactant of formula (1) is present in an amount of 0.1 to 20 wt %.

13. The method of claim 11, which further comprises a surfactant other than the compound of formula (1).

14. The method of claim 13, wherein the surfactant other than the compound of formula (1) is at least one surfactant selected from the group consisting of cationic, anionic, nonionic and amphoteric surfactants.

15. A method for shampooing hair, comprising:
applying the hair cleansing composition of claim 7 to the hair.

16. A hair cosmetic composition comprising an ether functional group containing cationic surfactant represented by formula (1):

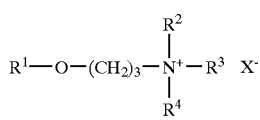

wherein,
$R^1$ represents a linear or branched $C_{6-24}$ alkyl or alkenyl group,
$R^2$ and $R^4$ each represents a $C_{1-6}$ alkyl group or $-(AO)_nH$ in which A represents a $C_{2-4}$ alkylene group and n is a number from 1 to 6 wherein individual A radicals are the same or different and are in any sequence,
$R^3$ represents a benzyl group or $-(A'O)_mH$ in which A' represents a $C_{2-4}$ alkylene group and m is a number from 1 to 6 wherein individual A' radicals are the same or different and are in any sequence, and
$X^-$ represents an anion.

17. A hair cosmetic composition, comprising:
(a) from 0.1 to 20 wt % of an ether functional group containing cationic surfactant represented by formula (1):

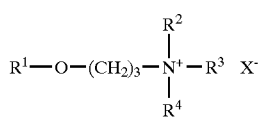

(1)

wherein, $R^{1'}$ represents a linear or branched $C_{6-24}$ alkyl or alkenyl group, $R^2$ and $R^4$ each represents a $C_{1-6}$ alkyl group or —$(AO)_nH$ in which A represents a $C_{2-4}$ alkylene group and n is a number from 1 to 6 wherein individual A radicals are the same or different and are in any sequence, $R^3$ represents a $C_{1-6}$ alkyl group, a benzyl group or —$(A'O)_mH$ in which A' represents a $C_{2-4}$ alkylene group and m is a number from 1 to 6 wherein individual A' radicals are the same or different and are in any sequence, and $X^-$ represents an anion; and (b) at least one surfactant other than the surfactant of formula (1) which is selected from the group consisting of cationic, anionic, nonionic and amphoteric surfactants.

18. A method for treating hair, comprising:

applying a hair cosmetic composition comprising:

(a) from 0.1 to 20 wt % of an ether functional group containing cationic surfactant represented by formula (1):

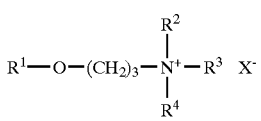

(1)

wherein, $R^{1'}$ represents a linear or branched $C_{6-24}$ alkyl or alkenyl group, $R^2$ and $R^4$ each represents a $C_{1-6}$ alkyl group or —$(AO)_nH$ in which A represents a $C_{2-4}$ alkylene group and n is a number from 1 to 6 wherein individual A' radicals are the same or different and are in any sequence, $R^3$ represents a $C_{1-6}$ alkyl group, benzyl group or —$(A'O)_mH$ in which A' represents a $C_{2-4}$ alkylene group and m is a number from 1 to 6 wherein individual A' radicals are the same or different and are in any sequence, and $X^-$ represents an anion, and (b) at least one surfactant other than the surfactant of formula (1) which is selected from the group consisting of cationic, anionic, nonionic and amphoteric surfactants, to the hair.

19. The hair cosmetic composition of claim 3, wherein the surfactant other than the compound of formula (1) is at least one surfactant selected from the group consisting of anionic, nonionic and amphoteric surfactants.

20. The method of claim 13, wherein the surfactant other than the compound of formula (1) is at least one surfactant selected from the group consisting of anionic, nonionic and amphoteric surfactants.

21. The method of claim 13, wherein the surfactant other than the compound of formula (1) is a cationic surfactant.

* * * * *

UNITED STATES PATENT AND TRADEMARK OFFICE
CERTIFICATE OF CORRECTION

PATENT NO. : 6,737,050 B2
DATED : May 18, 2004
INVENTOR(S) : Yasuhiro Doi et al.

It is certified that error appears in the above-identified patent and that said Letters Patent is hereby corrected as shown below:

Column 13,
Line 23, "0.1 to 2 wt %." should read -- 0.1 to 20 wt %. --

Signed and Sealed this

Twenty-third Day of November, 2004

JON W. DUDAS
*Director of the United States Patent and Trademark Office*